(12) United States Patent
Story et al.

(10) Patent No.: US 8,240,769 B1
(45) Date of Patent: Aug. 14, 2012

(54) MULTIPURPOSE LOWER EXTREMITY EXAMINATION STOOL

(76) Inventors: Adam Story, Saint Augustine, FL (US); Kurt K. Hubbard, St. Augustine, FL (US)

( * ) Notice: Subject to any disclaimer, the term of this patent is extended or adjusted under 35 U.S.C. 154(b) by 373 days.

(21) Appl. No.: 12/587,077

(22) Filed: Oct. 1, 2009

(51) Int. Cl.
  *A47C 16/00* (2006.01)
(52) U.S. Cl. ............ 297/423.41; 297/423.1; 297/423.14; 359/850; 359/857; 359/860; 359/863; 359/865; 600/247; 600/248; 600/592
(58) Field of Classification Search ............... 297/423.1, 297/423.14, 423.39–423.46; 359/850, 857, 359/860, 862, 863, 865, 882; 600/247, 248, 600/592
See application file for complete search history.

(56) References Cited

U.S. PATENT DOCUMENTS

| | | | | | |
|---|---|---|---|---|---|
| 907,420 | A | * | 12/1908 | Sollis ............................. | 359/855 |
| 1,643,626 | A | * | 9/1927 | May ............................... | 359/857 |
| 2,009,340 | A | * | 7/1935 | Edwards ........................ | 600/592 |
| 2,136,832 | A | * | 11/1938 | Weisberger ................... | 600/248 |
| 2,267,158 | A | * | 12/1941 | Locke ................................ | 34/90 |
| 2,382,131 | A | * | 8/1945 | Cameron ....................... | 359/860 |
| 3,533,671 | A | * | 10/1970 | Huber ............................ | 312/227 |
| 4,534,365 | A | * | 8/1985 | Bonetta et al. ................ | 600/592 |
| 5,139,036 | A | * | 8/1992 | Pickard ........................ | 132/73.5 |
| 5,501,682 | A | * | 3/1996 | Edwards-Cofie .............. | 601/61 |
| 6,392,823 | B1 | * | 5/2002 | Burnett ......................... | 359/803 |
| 6,598,992 | B1 | * | 7/2003 | Ames ............................ | 362/138 |
| 6,799,804 | B1 | * | 10/2004 | Fournier ................... | 297/423.41 |
| 6,834,655 | B1 | * | 12/2004 | Briscoe ......................... | 132/288 |
| 7,137,950 | B1 | * | 11/2006 | Murillo ......................... | 600/247 |
| 7,329,016 | B1 | * | 2/2008 | Shonk et al. .................. | 359/854 |
| 7,347,573 | B1 | * | 3/2008 | Isler .............................. | 359/854 |
| 7,354,110 | B1 | * | 4/2008 | Raghubir ................. | 297/423.45 |
| 2006/0245091 | A1 | * | 11/2006 | DeFazio ........................ | 359/879 |
| 2007/0091487 | A1 | * | 4/2007 | DeFazio et al. ............... | 359/859 |

* cited by examiner

*Primary Examiner* — Laurie Cranmer
(74) *Attorney, Agent, or Firm* — Mathew R. P. Perrone, Jr.

(57) ABSTRACT

A multipurpose, lower extremity, examination stool, has at least one light set in integral cooperation with at least one mirror to facilitate an examination of a foot by a person, a clinician, or a doctor. The foot examination stool preferably has a top mirror and a slide mirror. The slide mirror is slidably mounted below the top mirror and has a set of lights, to illuminate both the slide mirror and the lower extremity being tested or examined. The top mirror is illuminated by two sets of lights hingedly or rotatably mounted adjacently thereto and perpendicular to the slide mirror.

14 Claims, 8 Drawing Sheets

MULTIPURPOSE LOWER EXTREMITY EXAMINATION STOOL

This invention relates to an examination stool and more particularly to a multipurpose, lower extremity, examination stool, having lights and mirrors thereon, in integral cooperation to facilitate an examination of a lower extremity of a person, especially a foot.

BACKGROUND OF THE INVENTION

When a lower extremity of a person, especially a foot, that does not sense pain; the person to whom it belongs is at risk for damage to that foot. Such loss of sensation of pain requires immediate attention. Anything that facilitates reducing the dangers caused by that loss of ability to feel pain provides a great advantage. Due to the fact that having the foot examined requires a standing position, a sitting position or a lying position, a thorough examination of the foot can be difficult.

More particularly, when individuals with a diagnosis of diabetes, or a condition similar to that of diabetes, the person may lose sensation to the lower extremity. Thus, the person to whom the lower extremity belongs to has limited or no feeling, causing danger to the lower extremity. Such sensation loss requires immediate and consistent attention and monitoring. Anything that facilitates reducing damage, and thus further injury, provides a great advantage.

Because diabetes, tends to cause problems with the feet of a person, an especially careful examination of the feet of that person with diabetes may be required. In almost all instances, with any medical problem, the earlier diagnosis provides great advantages. This is especially true with diabetes and related problems. A device to facilitate that examination of the feet on anyone, especially a person with diabetes, can be very useful. Not only can a successful examination of feet be useful, it can also assist in the treatment of the person with diabetes.

Positioning a foot for examination provides a problem, because a foot and a leg to which it is attached can only move in a certain fashion. Yet many different foot movements are required to achieve the desired examination. With the movements of the foot for examination come many required body movements or other changes of position. It is very desirable to achieve the examination with reduced body movements, while relying on mostly foot movements in the hopes of reducing certain safety concerns that could put a person at risk for further injury. That further injury can come in many ways. Typical examples include falls and lack of monitoring, which may lead to the amputation of the foot or leg.

As a result of the movement required for the examination, the person being examined can be exhausted or tired. Firstly, a person suffering from diabetes is in a weakened condition. A difficult examination can further tire that person. Thus, it is very desirable to conserve energy for that person.

To that end many devices are known, which claim to facilitate examination of the foot. These devices tend to be either bulky and hard to use or an object that is too small. The too small problem causes the person to just put the object in the closet out of sight, and out of mind. Thus it becomes difficult to operate such a device, while examining a foot. It follows that a device, which is easy to use and reduces the required movements of a person having a foot examination, offers great advantages.

SUMMARY OF THE INVENTION

Among the many objectives of the present invention is the provision of an examination stool, having lights and mirrors thereon to facilitate an examination of a lower extremity, preferably of a human.

Another objective of the present invention is the provision of an examination stool, which is easy to operate.

Yet another objective of the present invention is the provision of an examination stool, which incorporates energy conservation for the person being examined.

Still another objective of the present invention is the provision of a multipurpose, lower extremity, examination stool, which provides work simplification for the user or clinician doing the examination.

A further objective of the present invention is the provision of a foot examination stool, which is not bulky nor easily misplaced.

A still further objective of the present invention is the provision of a foot examination stool, which does not compromise safety for a person being examined.

Yet a further objective of the present invention is the provision of a foot examination stool which reduces body movement required for a thorough foot exam facilitating proper body mechanics.

Yet another objective of the present invention is the provision of a foot examination stool, reduces body movement required for a foot exam.

Still another objective of the present invention is the provision of a multipurpose, lower extremity, examination stool, which reduces body movement required for the exam.

These and other objectives of the invention (which other objectives become clear by consideration of the specification, claims and drawings as a whole) are met by providing a multipurpose, lower extremity, examination stool, having lights mirrors in integrated cooperation to facilitate an examination of a lower extremity, especially a foot, by a person, a clinician or a doctor.

BRIEF DESCRIPTION OF DRAWINGS

Throughout the figures of the drawings, where the same part appears in more than one figure of the drawings, the same number is applied thereto.

DESCRIPTION OF THE PREFERRED EMBODIMENTS

Figure 1:
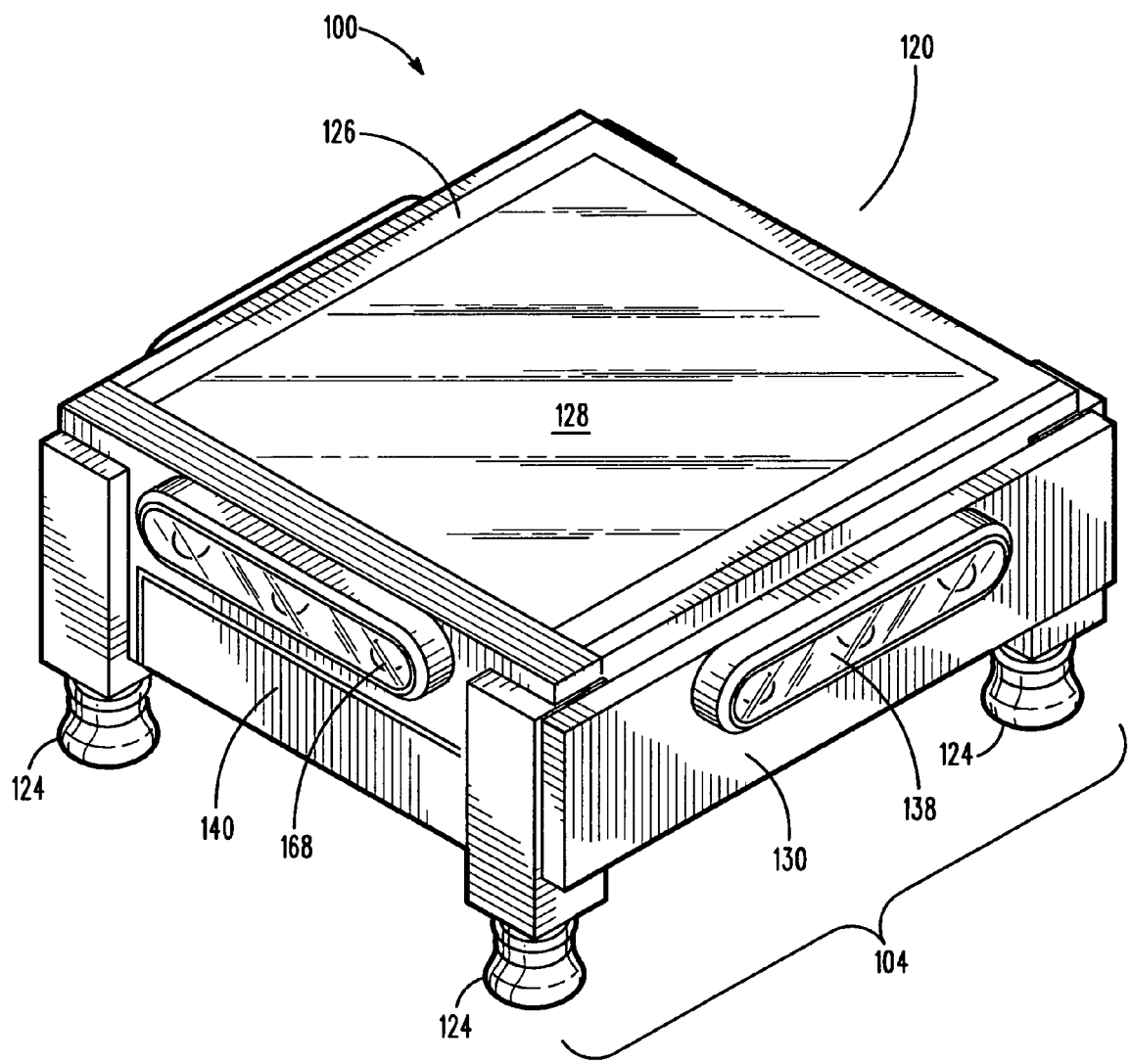
FIG. 1 depicts a top perspective view of multipurpose, lower extremity, examination stool 100 of this invention.
Figure 2:
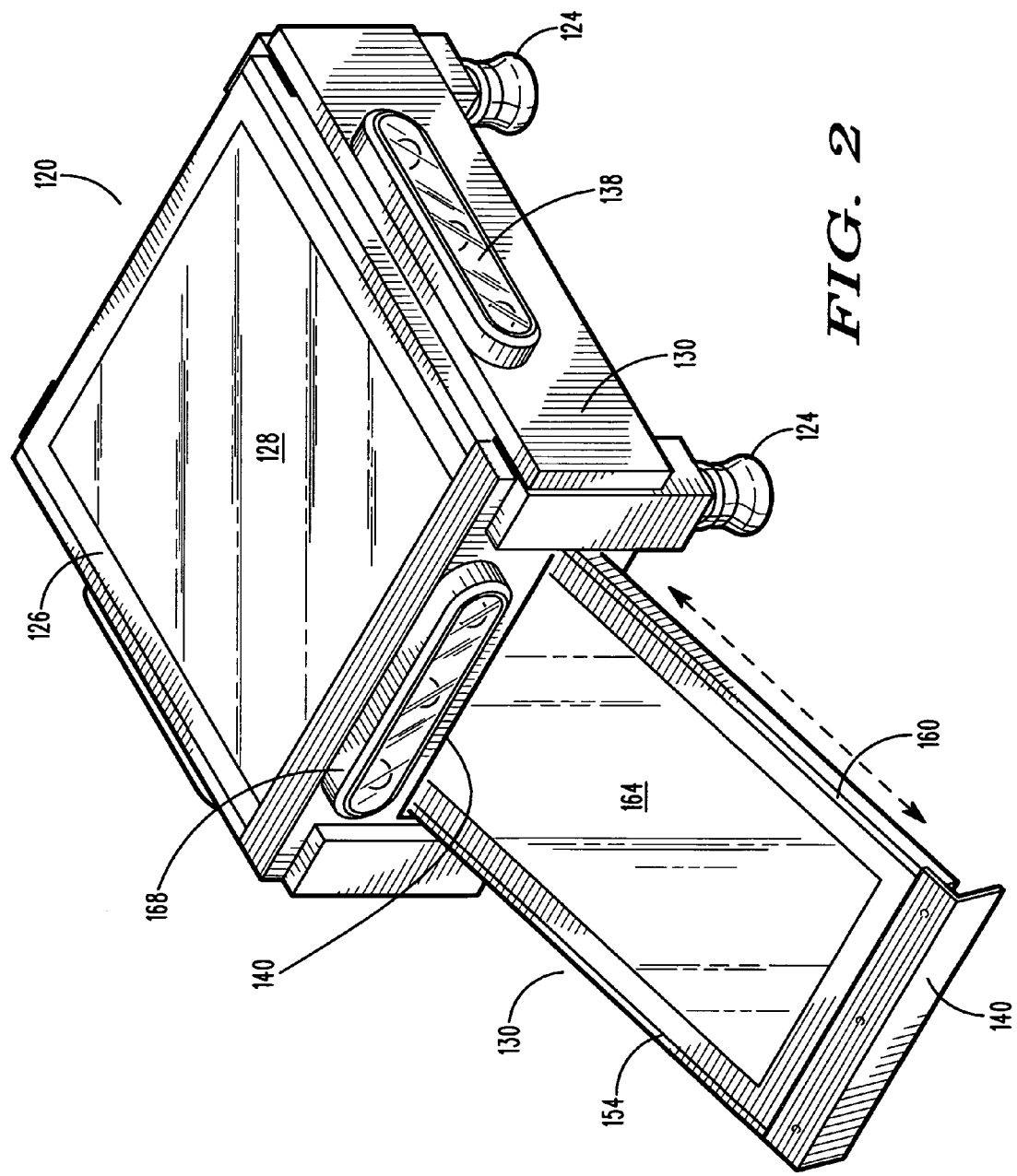
FIG. 2 depicts a perspective view of the multipurpose, lower extremity, examination stool 100 of this invention with slide mirror 164 being extended.

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, over, above, below, beneath, rear, and front, may be used with respect to the drawings. These and similar to directional terms are not to be construed to limit the scope of the invention in any manner. The words attach, connect, couple, and similar terms with their inflectional morphemes do not necessarily denote direct or intermediate connections, but may also include connections through mediate elements or devices.

The multipurpose, lower extremity, examination stool has at least one light set in integral cooperation with at least one mirror to facilitate an examination of a lower extremity, such as a foot, by a person, a clinician or a doctor. Clearly unless otherwise specified, multipurpose, lower extremity, examination stool; and foot examination stool may be used interchangeably. The at least one light set and the at least one mirror are relatively positioned, in order to facilitate the examination. This foot examination stool clearly forms a piece of Durable Medical Equipment (hereafter sometimes referred to as DME).

Preferably, the multipurpose, lower extremity, examination stool has a top mirror and a slide mirror mounted on or in a housing. The slide mirror is slidably mounted below the top mirror and has a set of lights, to illuminate the lower extremity or foot being tested. The top mirror is illuminated by two sets of lights rotatably, preferably with a hinge, mounted adjacently thereto and preferably perpendicular to the slide mirror.

The lights on the side and front of the lower extremity examination stool are used to make view the bottom of the foot better, especially for a person with low vision while doing a self exam. The side panel lights have a hinge to allow the light to be used as either a light for viewing the lower extremity or the bottom of the foot in the standing position, or for the equivalent of a night light illuminating the floor in order to avoid any tripping hazards. The front light is especially useful for illuminating the bottom of a foot for the angled component or sliding mirror. The sliding mirror is preferably used with a person being examined in the seated position. The multipurpose, lower extremity, examination stool is especially suitable for the examination of the human foot, suffering any type of injury. This examination can be applied to a person suffering from diabetes, or other lower extremity problem.

In FIG. 1, FIG. 2, FIG. 6, and FIG. 7, multipurpose, lower extremity, examination stool 100 has a housing 120 with a sliding member 160 mounted on the side thereof. Support housing 120 includes a set of preferably four legs 124 on a bottom portion thereof and a central mirror support 126 on a top portion thereof. Within central mirror support 126 is mounted a main mirror 128. Central mirror support 126 may include a tactile portion by the main mirror 128, in order to assist locating the main mirror 128 by touch or assist in the person testing the sensation of foot 102 or the lower extremity. Support housing 120 is preferably rectangular or square in shape.

Figure 3:
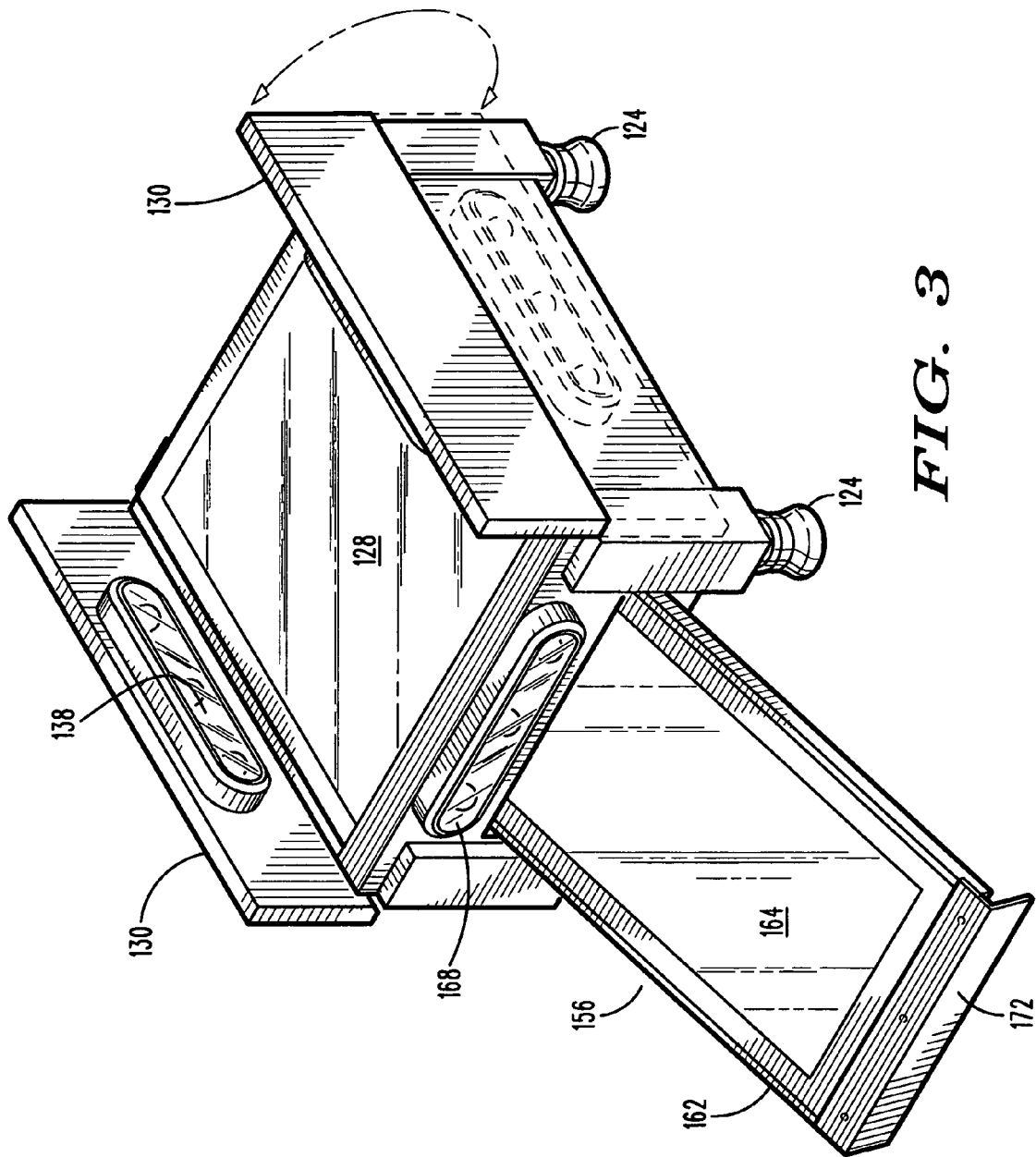
FIG. 3 depicts a perspective view of multipurpose, lower extremity, examination stool 100 of this invention with the hinged light assemblies 130 extended.
Figure 4:
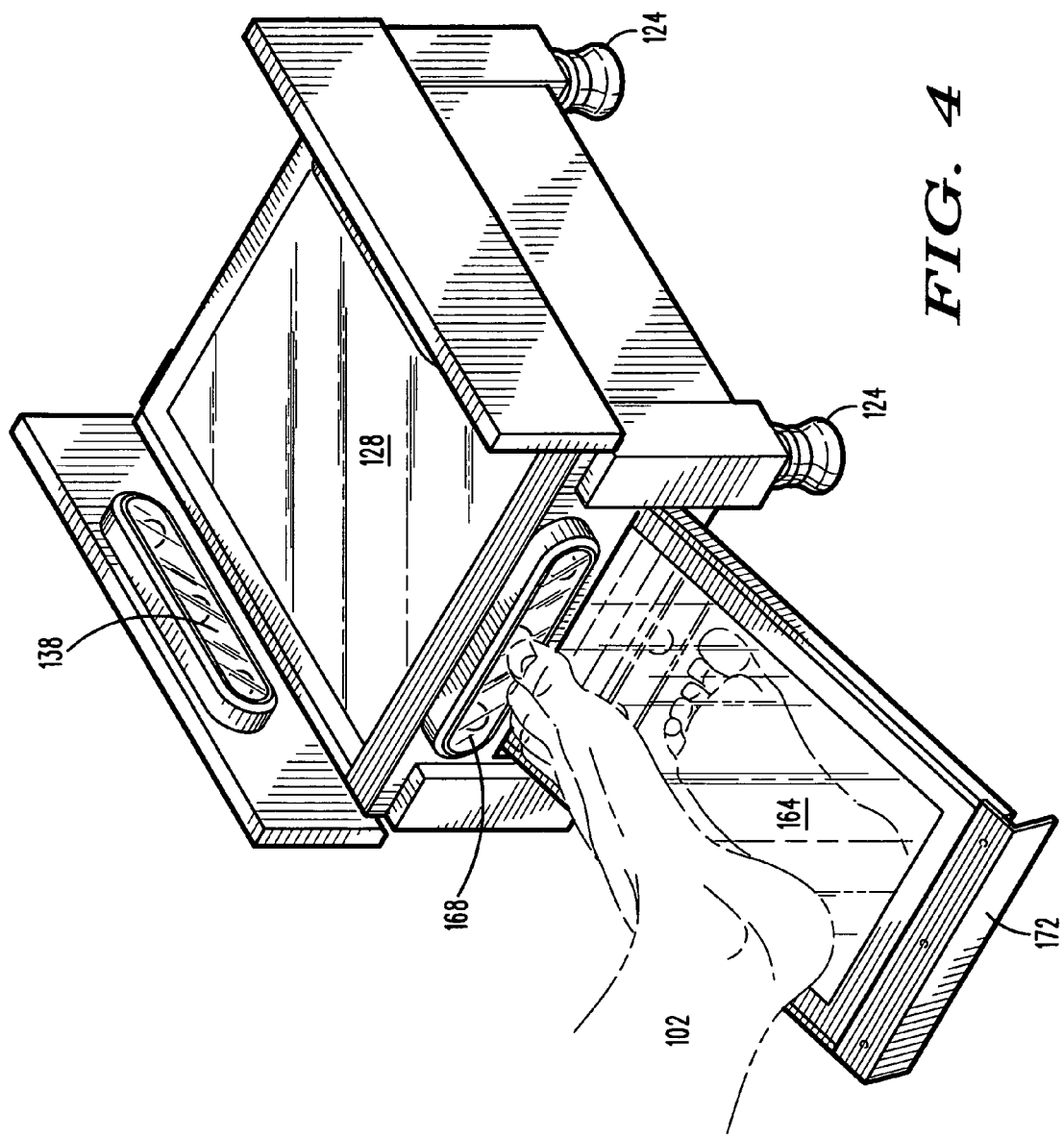
FIG. 4 depicts a perspective view of multipurpose, lower extremity, examination stool 100 of this invention with slide mirror 164 extended and in use.

Adding FIG. 3 to the consideration, adjacent to central mirror support 126 on opposing sides thereof are hinged light assemblies 130. Because each hinged light assembly 130 has a light housing 132 mounted on a hinge 134, the light assembly 130 provides illumination to main mirror 128 with lights 138 in main light housing 132. Each hinge 134 permits main lights 138 to move toward or away from main mirror 128 of central mirror support 126. With the movement of main lights 138, toward main mirror 128, it is possible to examine a lower extremity of a person, a foot 102 of that person placed thereon or close thereto.

Referring back to FIG. 1 and FIG. 6, perpendicular to each hinged light assembly 130 in support housing 120 is a slide port 140. Slide port 140 is on a side of support housing 120, and below the central mirror support 126. The slide port 140 receives the slide mirror 164. Slide mirror 164 may also have a tactile area adjacent thereto.

Figure 5:
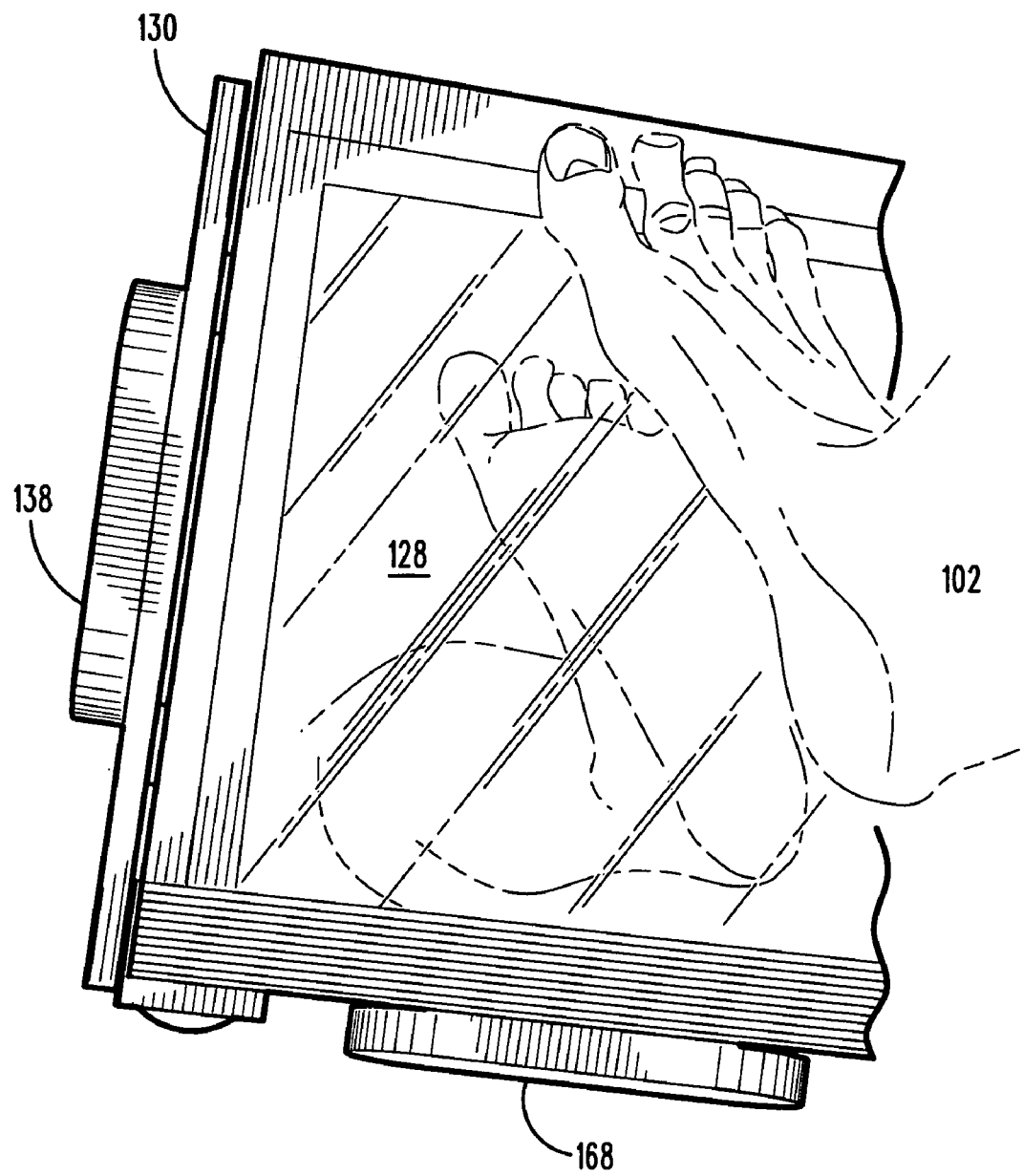
FIG. 5 depicts a top plan view of multipurpose, lower extremity, examination stool 100 of this invention with central mirror support 126 in use.
Figure 6:
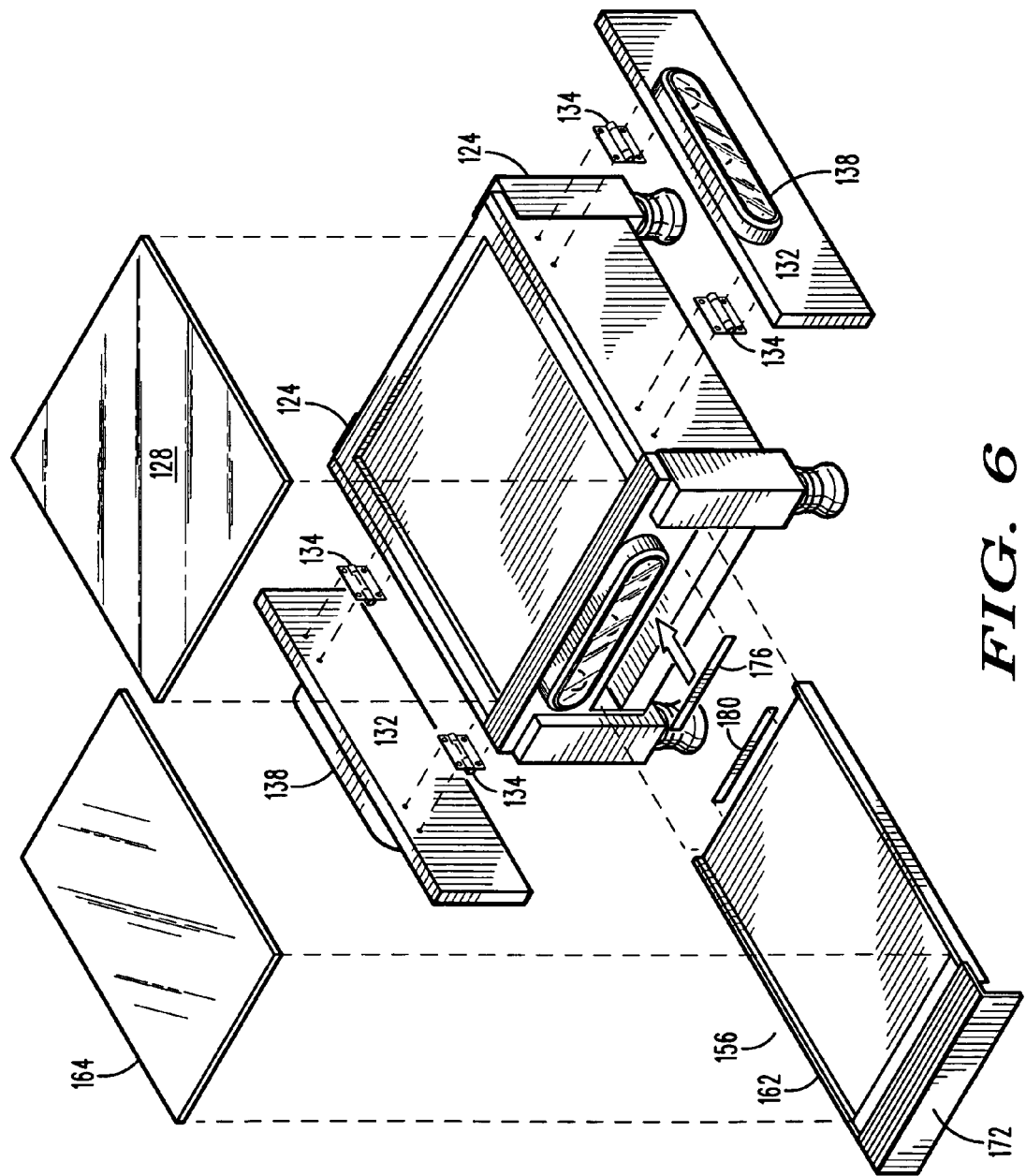
FIG. 6 depicts an exploded top perspective view of multipurpose, lower extremity, examination stool 100 of this invention.
Figure 7:
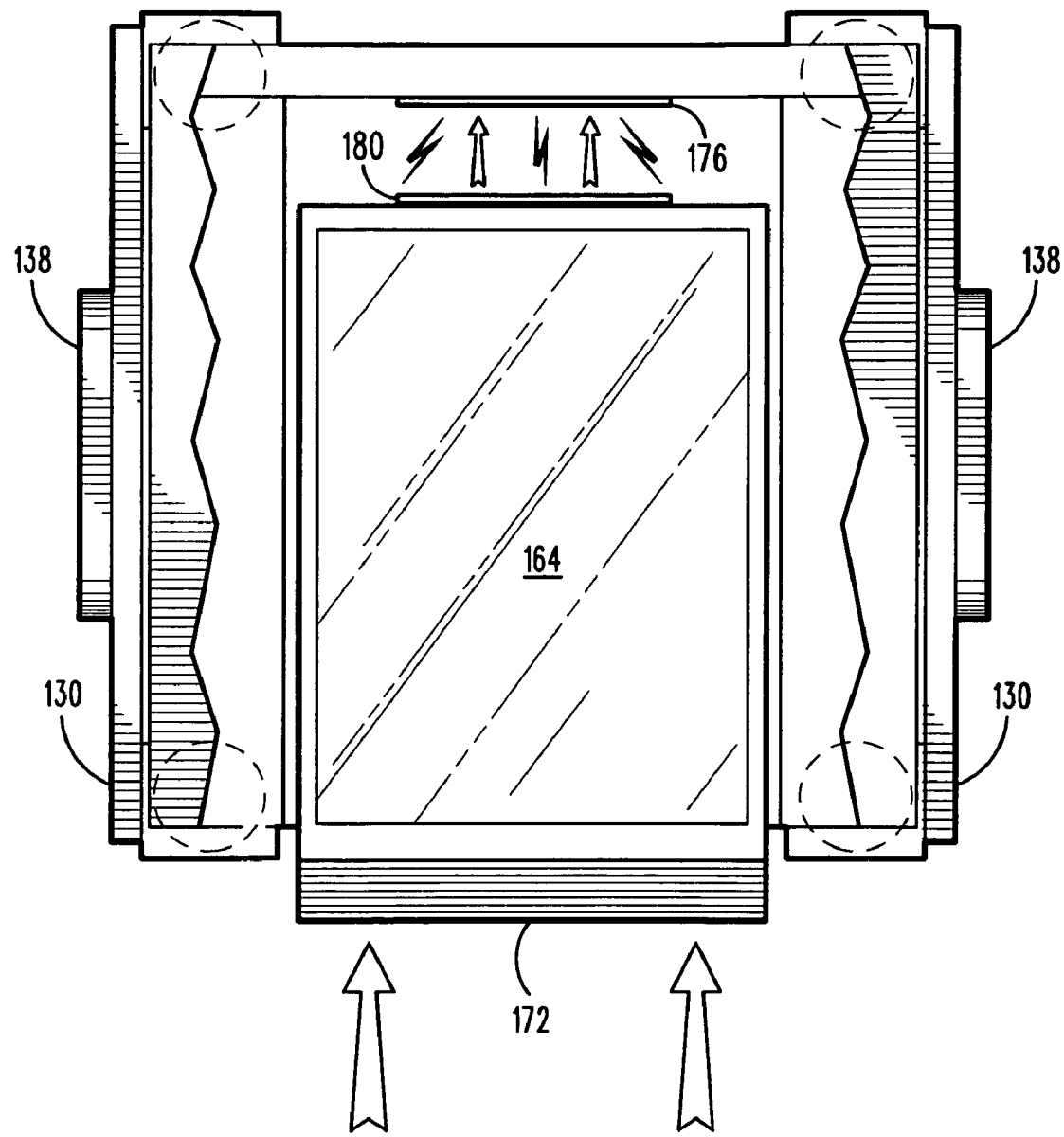
FIG. 7 depicts a top plan view of multipurpose, lower extremity, examination stool 100 of this invention.

With the further consideration of FIG. 5 and FIG. 6, the use of multipurpose, lower extremity, examination stool; or foot examination stool 100 becomes clear. A foot 102 is placed in close proximity to either main mirror 128, or slide mirror 164. Hinged or movable light assemblies 130 cooperate, jointly or severally, with top or main mirror 128 for the examination of foot 102. Slide light assembly 168 cooperates efficiently with slide mirror 164 for the examination of foot 102.

Sliding member 160 has a grip 172, which appears on the outside of support housing 120 when sliding member 160 is stored within support housing 120. Grip 172 facilitates moving sliding member 160 into support housing 120 for storage and transport of slide mirror 164. Side lights 168 facilitate use of slide mirror 164. A set of four legs 124 preferably provides the best support for foot examination stool 100.

Turning now to FIG. 6, on sliding member 160 oppositely from grip 172 is magnetic strip 180. Mounted within support housing 120 so that it will contact or be adjacent to magnetic strip 180 is metal strip 176. The contact or adjacent to position occurs when sliding member 160 is completely stored within support housing 120. This magnetic hold facilitates transport and storage of foot examination stool 100. Naturally, the positions of the magnetic strip 180 and the metal strip 176 can be reversed.

Grip 172, not only facilitates moving the sliding member 160 into and out of housing 120, but also supports slide mirror 164 in contact with the floor 104 (FIG. 1). The structure is well supported with the above described magnetic assemblies. Slide port 140 receives slide mirror 164 in port frame 154 slidably mounted within support housing 120 and below central mirror support 126. It is positioned above legs 124.

Mounted above slide port 140 are side lights 168 to cooperate with slide mirror 164. Side lights 168 are usually in a fixed position as opposed to main lights 138 with hinge 134.

Referring specifically to FIG. 6, an optional feature of examination stool 100 can be seen. Tactile area 156 has a tactile surface 162 framing slide mirror 164. Tactile surface 162 acts as a guide such that users with limited vision can feel where slide mirror 164 is located more readily. Tactile surface 162 has a series of indentations in the surface, which allow the user to feel that it is not the smooth surface of slide mirror 164. Tactile area 156 may also frame main mirror 128 in the same fashion.

In this preferred embodiment, the tactile surface 162 has a series of indentations to distinguish the tactile surface 162 from that of slide mirror 164 or main mirror 128. However, tactile surface 162 can be a series of raised knobs or bars, or any other suitable tactile structure that clearly distinguishes, by touch, the tactile surface 162 from the smooth surface of slide mirror 164 or main mirror 128.

Figure 8:
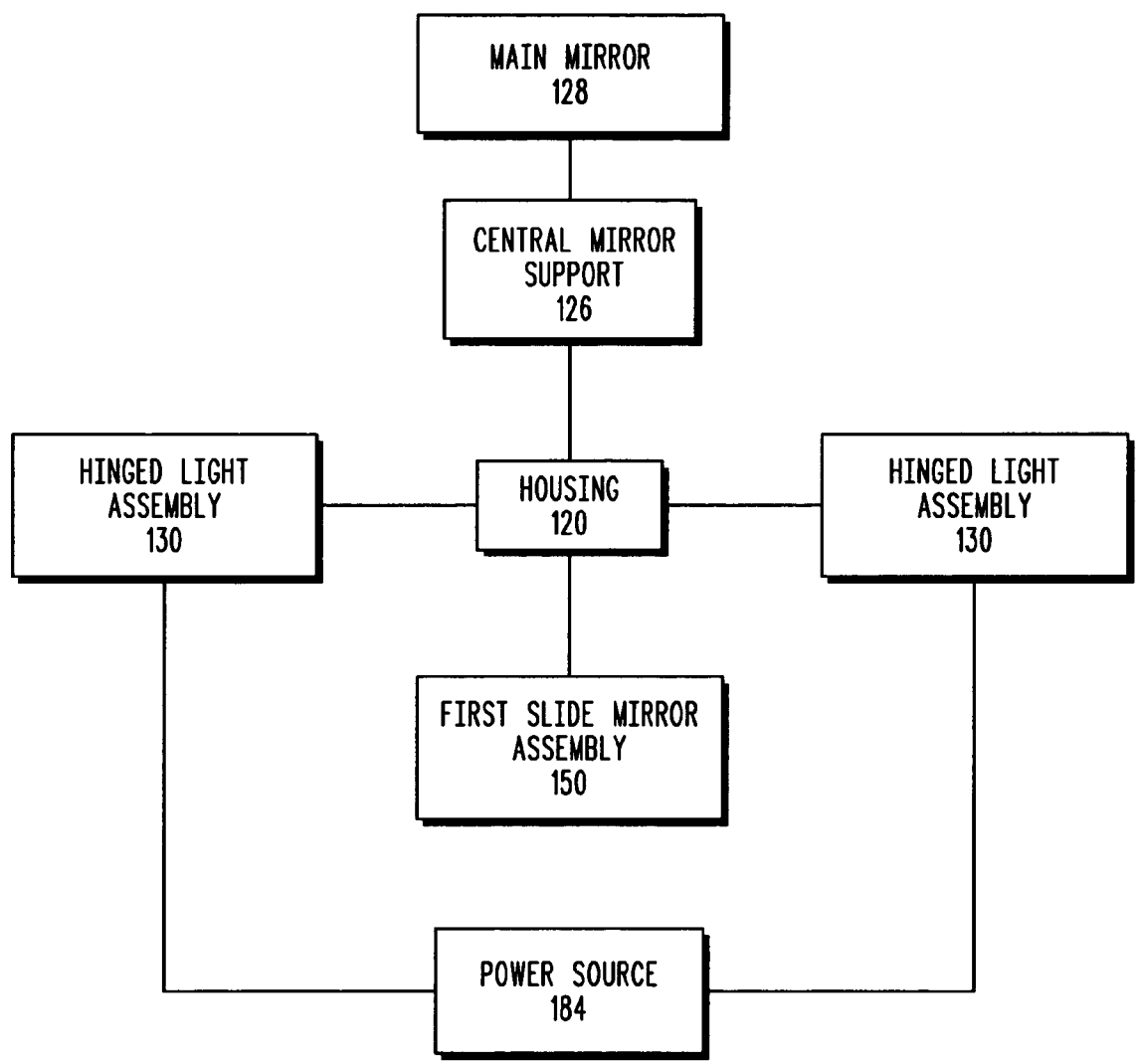
FIG. 8 depicts a block diagram of multipurpose, lower extremity, examination stool 100 of this invention.

In FIG. 8, variations in structure of the foot examination stool 100 may be more clearly seen. Foot examination stool 100 includes the housing 120 with the central mirror support 126, mounted thereon with the main mirror 128 contained therein. Light assemblies 130, preferably two in number, are mounted on opposing sides of the main mirror 128. Between the light assemblies 130 on one side is optionally, but preferably mounted first slide mirror assembly 150. First slide mirror assembly 150 may include sliding member 160 (FIG. 6) and side light assembly 168 (FIG. 6). Side light assembly 168 may optionally be mounted on housing 120 to cooperate with sliding member 160, which supports slide mirror 164.

Power source 184 is connected in standard fashion with side light 168, and main lights 138. Power source 184 may be based on direct electrical current or battery power, or standard alternating electrical current as desired. Side or front light assembly 168 or light assemblies 130 may be used to examine a lower extremity or as a nightlight. In this manner a foot may be examined in a darkened room or a lighted room as desired. With use as a nightlight, tripping or other undesired contact with foot examination stool 100 may be avoided.

This application—taken as a whole with the abstract, specification, claims, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this tool can become clear to a person having ordinary skill in this particular art. Such modifications are clearly covered by this disclosure.

What is claimed and sought to be protected by Letters Patent is:

1. A multipurpose, lower, extremity, examination stool, having at least one light set in integral cooperation with at least one mirror to facilitate an examination of a lower extremity comprising:
    a) the multipurpose, lower extremity, examination stool including a support housing to support the at least one light set and the at least one mirror;
    b) the at least one light set and the at least one mirror cooperating to facilitate the examination of a lower extremity of a person;
    c) the at least one light set or the at least one mirror being relatively movable to facilitate the examination;
    d) the at least one mirror including a top mirror supported on the support housing;
    e) the at least one light set being a first movable light set and a second movable light set;
    f) the first movable light set being oppositely disposed from the second movable light set;
    g) the first movable light set and the second movable light set jointly or severally working with the top mirror for an examination;
    h) the at least one mirror further including a slide mirror;
    i) the slide mirror being supported in the support housing;
    j) the slide mirror cooperating with a set of side lights;
    k) the slide mirror being mounted in a slide mirror assembly;
    l) the slide mirror assembly including a sliding member to support the slide mirror; and
    m) the slide mirror assembly being mounted in the support housing.

2. The multipurpose, lower extremity, examination stool of claim 1, further comprising:
    a) the support housing including a stool member;
    b) the support housing including a set of legs on a bottom portion thereof and a central mirror support on a top portion;
    c) the central mirror support mounting a main mirror; and
    d) the support housing being rectangular in shape.

3. The multipurpose, lower extremity, examination stool of claim 2, further comprising:
    a) the first movable light set including a first hinge to secure the first movable light set to the support housing;
    b) the second movable light set including a second hinge to secure the second movable light set to the support housing; and
    c) the first hinge and the second hinge permitting the first movable light set and the second movable light set to be moved toward or away from the main mirror.

4. The multipurpose, lower extremity, examination stool of claim 2, further comprising:
    a) the support housing including a slide port;
    b) the slide port being between the set of legs and the central mirror support; and
    c) the slide port including a holding means to releasably hold the slide mirror assembly in the support housing.

5. The multipurpose, lower extremity, examination stool of claim 4, further comprising:
    a) the sliding member having a grip to facilitate moving sliding member into the support housing for storage and transport of the slide mirror or out of the support housing for use of the slide mirror;
    b) the sliding member having a magnetized piece or a first magnet receptor mounted thereon and oppositely disposed from the grip to facilitate moving the sliding member into the support housing for storage and transport of the slide mirror or out of the support housing for use of the slide mirror; and
    c) a tactile surface framing the slide mirror and the main mirror.

6. The multipurpose, lower extremity, examination stool of claim 5, further comprising;
    a) the side lights facilitating use of the slide mirror;
    b) the set of legs being four legs; and
    c) the side lights and the second movable light being adapted to serve as a night light.

7. A foot examination stool to facilitate a foot examination, having at least one light set in, integral cooperation with at least one mirror to facilitate an examination of a foot comprising:
    a) the foot examination stool including a support housing to support the at least one light set and the at least one mirror;
    b) the at least one light set and the at least one mirror cooperating to facilitate the examination of the foot;
    c) the at least one light set and the at least one mirror being relatively movable to facilitate the examination;
    d) the foot examination permitting a foot examination with a reduced foot movement;
    e) the at least one mirror including a top mirror supported on the support housing;
    f) the at least one light set being a first movable light set and a second movable light set;
    g) the first movable light set being oppositely disposed from the second movable light set;
    h) the first movable light set and the second movable light set jointly or severally working with the top mirror to examine the foot;
    i) the at least one mirror further including a slide mirror;
    j) the slide mirror being supported in the support housing; and
    k) the slide mirror cooperating with a set of side lights;
    l) the slide mirror being mounted in a slide mirror assembly;
    m) the slide mirror assembly including a sliding member to support the first mirror; and
    n) the slide mirror assembly being mounted in the support housing.

8. The foot examination stool of claim 7, further comprising:
  a) the support housing including a stool member;
  b) the support housing including a set of legs on a bottom portion thereof and a central mirror support on a top portion;
  c) the central mirror support mounting a main mirror; and
  d) the support housing being rectangular in shape.

9. The foot examination stool of claim 8, further comprising:
  a) the first movable light set including a first hinge to secure the first movable light set to the support housing;
  b) the second movable light set including a second hinge to secure the second movable light set to the support housing; and
  c) the first hinge and the second hinge permitting the first movable light set and the second movable light set to be moved toward or away from the main mirror.

10. The foot examination stool of claim 9, further comprising:
  a) the support housing including a slide port;
  b) the slide port being between the set of legs and the central mirror support; and
  c) the slide port including a holding means to releasably hold the slide mirror assembly in the support housing.

11. The foot examination stool of claim 10, further comprising:
  a) the sliding member having a grip to facilitate moving sliding member into the support housing for storage and transport of the slide mirror or out of the support housing for use of the slide mirror;
  b) the sliding member having a magnetized piece or a magnet receptor mounted thereon and oppositely disposed from the grip to facilitate moving the sliding member into the support housing for storage and transport of the slide mirror or out of the support housing for use of the slide mirror; and
  c) a tactile surface framing the slide mirror and the main mirror.

12. The foot examination stool of claim 11, further comprising:
  a) the side lights facilitating use of the slide mirror;
  b) the set of legs being four legs; and
  c) the side lights, the first movable light set and the second movable light set being adapted to serve as a night light.

13. A method for conducting an examination of a lower extremity by providing an examination stool to facilitate an examination thereof comprising:
  a) providing the examination stool with at least one light set in integral cooperation with at least one mirror mounted on a support housing to facilitate an examination of a foot;
  b) conducting the examination on the examination stool with the at least one light set and the at least one mirror;
  c) moving the at least one light set and the at least one mirror to facilitate the examination;
  d) conducting the examination with a reduced movement of the lower extremity;
  e) providing the at least one mirror with a top mirror and a slide mirror supported on or in the support housing;
  f) providing the at least one light set with a first movable light set and a second movable light set;
  g) disposing the first movable light set oppositely from the second movable light set;
  h) the first movable light set and the second movable light set jointly or severally working with the top mirror to examine the lower extremity;
  i) providing the slide mirror with a set of side lights;
  j) providing the slide mirror with a slide mirror assembly;
  k) providing the slide mirror assembly with a sliding member and
  k) mounting the slide mirror assembly in the support housing.

14. The method of claim 13, further comprising:
  a) providing the support housing with a stool member;
  b) providing the support housing with a set of four legs on a bottom portion thereof and a central mirror support on a top portion;
  c) placing the top mirror in the central mirror support;
  d) providing a hinge for the first movable light set and a hinge for the second movable light set;
  e) moving the first movable light set and the second movable light set to be moved toward or away from the main mirror; and
  f) framing the slide mirror and the main mirror with a tactile surface.

* * * * *